United States Patent [19]

Kleemann et al.

[11] 4,356,323

[45] Oct. 26, 1982

[54] PROCESS FOR THE PRODUCTION OF 1-AMINO-PROPANEDIOL-(2,3) (I)

[76] Inventors: Axel Kleemann, Greifenhagenstrasse 25; Robert Nygren, Furstenbergstrasse 8; Rudolf Wagner, Furstenbergstrasse 6, all of 6450 Hanau 9, Fed. Rep. of Germany

[21] Appl. No.: 252,460

[22] Filed: Apr. 9, 1981

[30] Foreign Application Priority Data

Apr. 12, 1980 [DE] Fed. Rep. of Germany ....... 3014098

[51] Int. Cl.³ .................. C07C 89/02; C07C 91/10
[52] U.S. Cl. .................................. 564/475; 564/507
[58] Field of Search ............................ 564/475, 477

[56] References Cited

U.S. PATENT DOCUMENTS

| | | | |
|---|---|---|---|
| 2,373,199 | 4/1945 | Schwoegler et al. | 564/477 |
| 3,544,632 | 12/1970 | Haarer | 260/563 |
| 3,860,703 | 1/1975 | Wolff | 564/475 |

FOREIGN PATENT DOCUMENTS

| | | | |
|---|---|---|---|
| 544944 | 8/1957 | Canada | 564/475 |
| 694992 | 8/1940 | Fed. Rep. of Germany | 564/477 |
| 2339788 | 2/1974 | Fed. Rep. of Germany | 564/475 |
| 2421618 | 11/1975 | Fed. Rep. of Germany | 564/475 |
| 1941859 | 3/1976 | Fed. Rep. of Germany | 564/477 |
| 158167 | 1/1957 | Sweden | 564/477 |
| 760215 | 10/1956 | United Kingdom | 564/475 |

OTHER PUBLICATIONS

Sidgwick, "The Organic Chemistry of Nitrogen", pp. 95 and 96 (1966).
Knorr, Berichte Deutsche. Chem. Ges., vol. 32, pp. 750-757 (1899).
Baum, J. Org. Chem., vol. 27, pp. 2231-2233 (1962).

*Primary Examiner*—John Doll
*Attorney, Agent, or Firm*—Cushman, Darby & Cushman

[57] ABSTRACT

The production of 1-amino-propanediol-2,3 is attained with good yields and in an industrially simple manner by reacting liquid ammonia with glycidol under pressure.

13 Claims, No Drawings

PROCESS FOR THE PRODUCTION OF 1-AMINO-PROPANEDIOL-(2,3) (I)

BACKGROUND OF THE INVENTION

The production of 1-amino-propanediol-2,3 by the addition of ammonia to glycidol was first described by L. Knorr and E. Knorr (Ber. deutsch. Chem. Ges. Vol. 32, pages 750–757 (1899)). The authors employed thereby one part by weight of glycidol with 100 parts by weight of 25% aqueous ammonia and then obtained after working up by distillation 1-amino-propanediol-2,3 in a yield of 44% based on the glycidol employed. The weight ratio of glycidol to aqueous ammonia (25%)=1:100 means a mole ratio of glycidol to ammonia=1:109.

This method of production of 1-amino-propanediol-2,3 was examined by K. Baum and W. T. Maurice (J. Org. Chem. Vol. 27, pages 2231–2233 (1962)), in which case under the same conditions they obtained a yield of 68% theory. This better yield is based on the fact that the first mentioned authors distilled the reaction product at 235°–250° C./320 mm, while the last mentioned authors carefully distilled, namely at 80°–106° C./0.1–0.15 mmHg and therewith did not cause loss through thermal decomposition.

While the last named process also brings about better yields compared to the process of Knorr (loc. cit.), the amounts of aqueous ammonia supplied to the cycle represents a considerable load in the industrial carrying out of the process.

Besides, it requires a very large reaction space because of the above-mentioned molar ratio of glycide to ammonia, as well as a distillation plant for the concentration of the diluted aqueous ammonia solution supplied to the cycle.

The object of the invention, therefore, is the development of a process for the production of 1-amino-propanediol-2,3 in good yields and in an industrially simple manner.

SUMMARY OF THE INVENTION

It has now been found that the reaction of glycidol with ammonia in homogeneous liquid phase with good yields and without particular industrial expense can be carried out if glycidol and liquid ammonia are reacted together under such pressure that the ammonia remains liquid.

In general, the molar ratio of glycidol to liquid ammonia is in the range of 1:5 to 15.

Preferably, there is a molar ratio 1:10.

Molar ratios below 5:1 (liquid ammonia to glycidol) are indeed possible; however, the yields of amino-propanediol obtained are reduced through the increased formation of the bis-products.

Above a ratio of 15:1, there does not occur an essential increase in yields; however, then the time-space yields are reduced.

Since the process of the invention is operated without the presence of a solvent, as was previously customary, the necessary recycling of the liquid ammonia is made much easier. Besides, there are eliminated plants for the concentration of aqueous ammonia as in the process of Baum and Maurice (loc. cit.).

Simultaneously, there is a considerable increase in the space-time-yield compared to the previously known process; in the above-mentioned prior art process (loc. cit.), it amounts to 360 l/kg×h while according to the invention this can be increased by about a factor of about 60 and consequently there is only needed a reactor of 6 liters capacity for the production of 1 kg of aminopropanediol per hour.

The pressure range is between 8 and 150 bar, preferably 20 to 90 bar.

The yields now produced in comparison to Baum and Maurice (loc. cit.), namely in the absence of a solvent, i.e., diluting agent, furthermore are surprising since glycidol is inclined to self condense as a bifunctional compound. Therefore, it must have been expected on the contrary that in the absence of a solvent the yield would be greatly reduced on account of self condensation.

The reaction temperature is 20° to 180° C., preferably 50° to 120° C.

1-Aminopropanediol-2,3 is an industrially interesting product for the production of X-ray contrast agents, see Belgian Pat. No. 855,580, inflammation arresting agents, see German OS No. 2339788, agents against illnesses of birds, e.g., chickens, see U.S. Pat. No. 3,860,703, for analgesics, see British Pat. No. 1072359 and cosmetics, see German OS No. 2421618.

Unless otherwise indicated, all parts and percentages are by weight.

The process can comprise, consist essentially of, or consist of the steps set forth with the stated materials.

The invention will be explained in more detail in connection with the following examples.

DETAILED DESCRIPTION

Experimental Apparatus

The following examples were carried out in the following experimental apparatus.

By means of two pumps, regulated amounts of the reactants were conveyed into the reactor from a supply reservoir filled with glycidol and a pressure flask containing liquid ammonia. This consisted of a double jacketed tube wherein the outer jacket space serves, with the help of water, to bring the reaction mixture in the inner tube to the desired temperature and to carry off the heat of reaction. The reaction was carried out in liquid, homogeneous phase. The pressure needed to liquify the reaction was held through a pressure control valve at the end of the double jacketed tube. The inner tube, thus the reaction zone, had a volume of 4.2 liters. After passing through the reaction zone, the reaction mixture was relieved of pressure at the pressure control valve and led into a reservoir. Hereby, there escaped from the crude product up to over 99% of the ammonia employed in excess, which after condensation, could again be supplied to the reaction. From the crude product, the 1-aminopropanediol was recovered by fractional vacuum distillation.

EXAMPLE 1

There were dosed into the above-mentioned reactor at 85° C. and 45 bar per hour 0.65 kg of glycidol and 2.23 kg of liquid ammonia. (Molar ratio glycidol:ammonia=1:15). After working up the reaction product by distillation, there were obtained 0.55 kg of aminopropanediol per hour, corresponding to 69% of theory, based on the glycidol employed. Boiling point: 94° C. (0.2 Torr), purity $\geq$ 99.5% (amine titration).

EXAMPLE 2

There were dosed into the above-mentioned reactor at 70° C. and 35 bar per hour 0.53 kg of glycidol and 1.25 kg of liquid ammonia (Molar ratio glycidol:ammonia=1:10.1). After working up the reaction product by distillation, there were obtained 0.4 kg of aminopropanediol per hour, corresponding to 62% of theory, based on the glycidol employed.

EXAMPLE 3

There were dosed into the above-mentioned reactor at 80° C. and 40 bar per hour 1.2 kg of glycidol and 1.3 kg of liquid ammonia. (Molar ratio glycidol:ammonia=1:5). After working up the reaction product by distillation, there were obtained per hour 0.77 kg of aminopropanediol, corresponding to 52% of theory, based on the glycidol employed.

EXAMPLE 4

There were dosed into the above-mentioned reactor at 60° C. and 25 bar per hour 0.3 kg of glycidol and 1.0 kg of liquid ammonia. (Molar ratio glycidol:ammonia=1:14.8). After working up the reaction product by distillation, there was obtained 0.25 kg of aminopropanediol per hour, corresponding to 69% of theory, based on the glycidol employed.

In Examples 2–4 also the boiling point and the purity of the product correspond to the data given in Example 1.

The entire disclosure of German priority application No. P 3014098.8-42 is hereby incorporated by reference.

The process can be carried out under anhydrous conditions and in the absence of solvent.

What is claimed is:

1. In a process for the production of 1-aminopropanediol-2,3 by the reaction of glycidol with ammonia the improvement comprising reacting glycidol and liquid ammonia under pressure sufficient to keep the ammonia in liquid form.
2. A process according to claim 1 wherein the glycidol and liquid ammonia are employed in a molar ratio of 1:5 to 15.
3. A process according to claim 1 wherein the glycidol and liquid ammonia are employed in a molar ratio of 1:10.
4. A process according to claim 1 wherein the reaction is carried out at a pressure of 8 to 150 bar.
5. A process according to claim 2 wherein the reaction is carried out at a pressure of 8 to 150 bar.
6. A process according to claim 1 wherein the reaction is carried out at 20 to 90 bar.
7. A process according to claim 2 wherein the reaction is carried out at 20 to 90 bar.
8. A process according to claim 3 wherein the reaction is carried out at 20 to 90 bar.
9. A process according to claim 7 wherein the temperature is 50° to 120° C.
10. A process according to claim 1 carried out under anhydrous conditions in the absence of a solvent.
11. A process according to claim 1 wherein the materials employed consist essentially of glycidol and liquid ammonia.
12. A process according to claim 1 wherein the materials employed consist of glycidol and liquid ammonia.
13. A process according to claim 12 wherein the glycidol and liquid ammonia are employed in a molar ratio of 1:5 to 1:15, the pressure is 8 to 150 bar and the temperature is 50° to 120° C.

* * * * *